(12) United States Patent
Bennett

(10) Patent No.: US 7,537,007 B2
(45) Date of Patent: May 26, 2009

(54) METHOD OF INERTING HIGH OXYGEN CONCENTRATIONS

(76) Inventor: Joseph Michael Bennett, 1020 Kellyn La., Hendersonville, TN (US) 37075

( * ) Notice: Subject to any disclaimer, the term of this patent is extended or adjusted under 35 U.S.C. 154(b) by 710 days.

(21) Appl. No.: 10/836,570

(22) Filed: May 1, 2004

(65) Prior Publication Data
US 2004/0226725 A1 Nov. 18, 2004

Related U.S. Application Data

(60) Provisional application No. 60/467,106, filed on May 1, 2003.

(51) Int. Cl.
*A61M 11/00* (2006.01)
(52) U.S. Cl. .............................. 128/202.24; 128/207.18
(58) Field of Classification Search ............ 128/203.12, 128/202.25, 202.24, 200.24, 207.18
See application file for complete search history.

(56) References Cited

U.S. PATENT DOCUMENTS

| | | | |
|---|---|---|---|
| 3,715,438 A | 2/1973 | Huggett | |
| 3,840,667 A | 10/1974 | Huggett | |
| 3,893,514 A | 7/1975 | Carhart et al. | |
| 5,040,609 A | 8/1991 | Dougherty, Jr. et al. | |
| 5,117,917 A | 6/1992 | Robin et al. | |
| 5,228,434 A * | 7/1993 | Fishman | 128/203.12 |
| 6,382,207 B1 * | 5/2002 | Giuffre et al. | 128/202.24 |
| 6,637,434 B2 * | 10/2003 | Noble | 128/207.18 |

* cited by examiner

*Primary Examiner*—Steven O Douglas

(57) ABSTRACT

A system for protecting individuals and property exposed to potential ignition and fires resulting from the release of high-oxygen concentration gas blends from oxygen systems used for breathing assistance. Said system comprises an oxygen storage container and delivery mechanism, said container filled with a blend of above-atmospheric oxygen and inert gases of appropriate composition and capacity to prevent the onset of ignition and fire when discharged and encountering ignition sources and combustibles, yet suitable for breathing by recipients and users of the system. Alternative embodiments can comprise covers over said oxygen containers, filled with materials suitable to prevent the ignition of combustibles encountering the high-oxygen blends from said oxygen containers, when both the blends and materials are dually discharged due to rupture of their respective containers after experiencing an impact.

20 Claims, 1 Drawing Sheet

METHOD OF INERTING HIGH OXYGEN CONCENTRATIONS

This application claims the benefit of provisional patent application 60/467,106, filed May 1, 2003 and is incorporated by reference.

BACKGROUND OF THE INVENTION

1. Field of the Invention

The present invention relates to a method of producing an inert gas mixture. More specifically, the present invention relates to rendering a high-oxygen gas mixture inert to prevent the occurrence of fire if exposed to an ignition source. This feature is particularly valuable when applied to medical applications, such as during surgery or home health care, where high oxygen levels are necessary during medical procedures or health-impaired conditions.

2. Related Art

Surgery room fires, which occur when breathable high-oxygen blends administered to patients come into contact with local combustible materials and tissues, and ignition sources such as laser tools and cauterizers, result in patient injuries or fatalities that are not that uncommon. This serious situation has been recently discussed in several national television documentary programs, as attested by the following quote from the "OSHA Compliance" website (www.osha-compliance.com):

> "Recently, the popular news program "60 Minutes" ignited the fears of the American public by demonstrating how easily fires can occur during routine surgery. Of the several hundred surgical fires that occur each year, more than a few result in serious harm to the sedated patient."

The rationale for the high risk of fire in this situation is that patients require large relative concentrations of oxygen to breathe, sometimes 30-55% by volume or greater, when their constitution is weak during surgery or with other debilitating pulmonary illnesses, and such a high oxygen concentration makes a myriad of materials easy to ignite, and very difficult to prevent from igniting. Fires can often occur within the windpipe and lungs of a patient, due to laser tools or during cauterization while performing a routine tracheotomy or similar procedures. When this occurs, surgeons often instinctively move back from the flash fire, then after gathering their bearings, attempt to quench the fire by closing the wound from the outside to try to starve it. Unfortunately, the oxygen is already present within the burning region, and by the time the hazard is brought under control, severe pulmonary or other regional burn injuries have occurred, which either result in fatalities, or painful, debilitating injuries. It is also common that oxygen can leak underneath the breathing mask, and accumulate around operating table curtains and other combustible textile materials, which exposed to a high oxygen source can facilitate ease of ignition under circumstances where ignition could not occur in normal atmospheric conditions.

This hazard is also present where oxygen tanks are used in a home health care environment, with approximately 4 million individuals using such equipment in the U.S. In this circumstance, other ignition sources are commonly present, such as cigarettes and other electrical equipment, and numerous residential fire department calls respond to such catastrophic fire events. For these applications, high oxygen concentrations may also be employed, comparable to operating room applications; however the likelihood of ignition and fire may be even higher in this circumstance due to less control over the combustibles exposed in the environment, as well as minimal training of users as to the proper procedures for use of such oxygen equipment.

It is extremely difficult to identify classes of gaseous compounds that can be added to high-concentration oxygen mixtures and accomplish inertion against ignition when the mixture is applied to significant ignition sources and combustible materials, at inertant concentrations that still retain a sufficient oxygen concentration needed for most of these applications in normal use. It is even more difficult to identify classes of compounds that are successful inertants under such restrictions, and yet are sufficiently safe to breathe in the required inerting concentrations for humans during normal use, including individuals with less than ideal health.

Carhart et al (U.S. Pat. No. 3,893,514) discloses a means of suppressing fires in confined spaces, by sealing the chamber and discharging super-pressurized nitrogen into the chamber, at a sufficient quantity to extinguish fires, at a final chamber pressure of 1.5 to 2 atmospheres. This approach exploits the principle by which humans and other mammals require a minimal partial pressure of oxygen of 0.2 to 0.3 atmospheres to normally function, regardless of the local pressure, while fires require a minimum oxygen relative atmospheric concentration of 10-15% to be sustained. By discharging nitrogen to generate excess atmospheric pressure, the relative oxygen concentration can drop below this level to prevent the sustainment of fires, yet retain the minimal partial pressure of oxygen to sustain human occupation. No mention is made of effectively extinguishing or preventing fires at elevated oxygen levels required for medical applications, and some surgical operations require access to the airways of the patient that would preclude containment and sustainment of the volume at high pressures.

Dougherty et al discloses (U.S. Pat. No. 5,040,609) the use of compositions containing $CHF_3$ as a means of preventing or extinguishing fires. It can be used in compartments in volume percentages as high as 80% in a safe manner for human exposure, at least as claimed at the time by the applicants. It is disclosed solely for use in compartments, and not administered directly to humans. It is also disclosed as for use in normal atmospheric air conditions, and not in elevated oxygen compositions. In fact, in calculations disclosed in the application, it is seen that the lower effectiveness of the chemical results in the requirement of 62% concentration in air to prevent or suppress fires, with only 21% of oxygen present, with minimal further expansion of the permitted oxygen concentration, as the required chemical concentration would then require even greater amounts.

Robin et al discloses (U.S. Pat. No. 5,117,917) a range of perfluorinated products, of the chemical family $C_xF_{2x+2}$, that are disclosed to address pre-existing fires. This family of chemicals, and in particular $C_4F_{10}$, are disclosed as being efficient in extinguishing files, while also exhibiting no ozone depletion and low toxicity. It was not disclosed whether the chemical(s) could be applied to high oxygen environments, or directly to a human subject.

Huggett discloses (U.S. Pat. No. 3,715,438) a means of using perfluorocarbon chemicals to prevent and control fires, by mixing them in appropriate quantities with air, in a manner to create habitable atmospheres and sustain mammalian life. To determine the correct amount of inertant required to prevent combustion, Huggett established that atmospheric mixtures that exhibit a threshold heat capacity of 40-50 cal/C (dependent upon the flammability of the present combustibles) per mole of oxygen present have too much heat absorptive capability to permit a fire to be sustained. To produce an atmospheric blend of these specifications, Huggett devised a formula to determine the quantities of various inertants that could raise the bulk heat capacity to that level (with greater quantities reducing the oxygen level). He found that the high heat capacity perfluorocarbons were an ideal candidate for consideration, exhibiting high heat capacities, low boiling points and very low toxicity. The scope of Huggett's analysis was producing a non-combustible atmosphere at an oxygen level comparable to that normally encountered on Earth—i.e., 19-21% oxygen blended atmospheres. He analyzed exclusively atmospheres beginning with normal air, with dilution due to the addition of the perfluorocarbon inertant, and in some cases the addition of some "make-up" oxygen to restore the blend to near-normal terrestrial conditions of oxygen concentration. At oxygen concentrations of that level, as little as 5.2 to 12.6% of perfluoropropane was necessary (corresponding to threshold heat capacities of 40 to 50 cal/C, respectively) to inert atmospheres with final oxygen concentrations of 21% (the same as normal air). Huggett defined the "habitable" conditions of his scope as those permitting "normal" activities for occupants. The "makeup" oxygen, when employed, was to replenish oxygen respirated in the closed, hermetic system, as opposed to a steady feed system. In the discussion of safe oxygen partial pressures, it was stated that is was understood (at the time) that a range from 1.8 psia to 8.2 psia were the limits of safe exposure, which was mentioned in context since at the time in the Space Program, such a maximum total pressure of pure oxygen was used in the atmosphere of the Lunar Modules at the time. It was mentioned in the context of preferring an "ideal" oxygen level of 18-21% for Huggett's embodiment, for "normal" activities of the scope of his invention. In summary, the specification and claims of Huggett reveal several characteristics—(1) they are all focused on modified "air"-based atmospheres that feature a significant component of nitrogen; (2) the focus of the specifications and totality of the claims focuses on maintaining merely "sufficient" oxygen to sustain mammalian life, which by his definition provides an atmosphere to permit occupants to conduct "normal" activities for extended periods, elaborated in the text as being preferentially 18-21%, (3) only perfluorocarbons and nitrogen are mentioned as inertant components under consideration, (4) any "make-up" oxygen is supplied to sustain this "sufficient" amount that is otherwise lost due to respiration or other losses, (5) discharge is expected to be a single event, with "make-up" oxygen only applied as needed to restore steady conditions in the enclosure, as opposed to a steady flow of blended atmosphere to the subject, and (6) all the claims and discussion refer to deployment of this atmosphere within an entire enclosure, versus being administered directly to a human being.

Huggett also discloses (U.S. Pat. No. 3,840,667) a follow-on application that elaborates further on this approach. In it, it discloses adding helium as the primary component within the specification, and as an essential component of every claim, purportedly to add a low-molecular weight additive to the other high-molecular weight inertant to bring the overall average molecular weight to that more closely approaching that of regular air, presumably for increased comfort of those exposed to it. A range of oxygen partial pressures was disclosed to facilitate the invention's use in a wide variety of atmospheric pressures, from sub-atmospheric on space platforms, to above atmospheric in hyperbaric chambers, but at an overall oxygen concentration within the "optimal" limits for comfort for normal activities.

In summary, it is desired to provide a system and special-purpose, artificial composition of oxygen and other compounds (rather than air-based derivatives), including various components other than just perfluorocarbons, that render the composition inert and unable to support ignition and flame when exposed to ignition sources and combustible materials, with oxygen volumetric concentrations in the composition of at least 30-55% or more, which is needed for medicinal and recuperative processes that extend beyond "normal" activities, and the levels of oxygen concentration required to perform them. Additionally, such a composition and system must be designed so as to also support human (or mammalian) life when it is administered directly to an individual, typically in a medical application, in a manner providing steady flow to the subject, although other applications such as manned space platforms, submarines and other enclosed spaces are possible. No technique has been demonstrated that incorporates these features previously, in their entirety.

SUMMARY OF THE INVENTION

The principle object of the present invention is to provide a system and a variety of inert compositions of gases as an artificial atmosphere discharged from said system that do not support ignition and combustion when exposed to ignition sources and combustible materials.

Another object of the invention is to provide an inert gas composition that features a relative oxygen volumetric concentration of 30% or more.

Another object of the invention is to provide an inert gas composition that is safe for individuals or mammals to breathe for an indefinite period.

Another object of the invention is to provide a system that can administer said inert compositions directly to the subject, using direct respiratory assistance equipment administering said inert composition in a steady manner.

The foregoing objects can be accomplished by providing certain classes of compounds to an oxygen or oxygen and nitrogen mixture that accomplish the aforementioned objects, including accomplishing inertion to prevent the support of ignition and fire, permitting the volumetric concentration of oxygen of 30% or more while administrating directly to individuals for medicinal or other purposes, and yet be a sufficiently non-toxic composition to permit its safe use for individuals when administered for an indefinite period, packaged in a system to administer directly to a subject in a steady process via respiratory equipment, or alternatively in an enclosure as a novel composition. Although this disclosure is intended to disclose the unprecedented application of such new compositions in general for applications and features never before disclosed to provide fire safety for these applications, many possible compositions are potentially available now and in the future, and specific composition ingredients can be identified now as preferred embodiments at this time as representatives of the many compounds and combinations possible now and in the future. These current compounds include the perfluorocarbon family of compounds, which have been shown to feature such inertion and low toxicity characteristics in published data, including in oxygen-enriched environments, and many others, including fluoroethers. Thus is described a system that can satisfy all of the objects stated previously, whereas prior art cannot satisfy all of the objects in their entirety.

DETAILED DESCRIPTION

Figure 1:
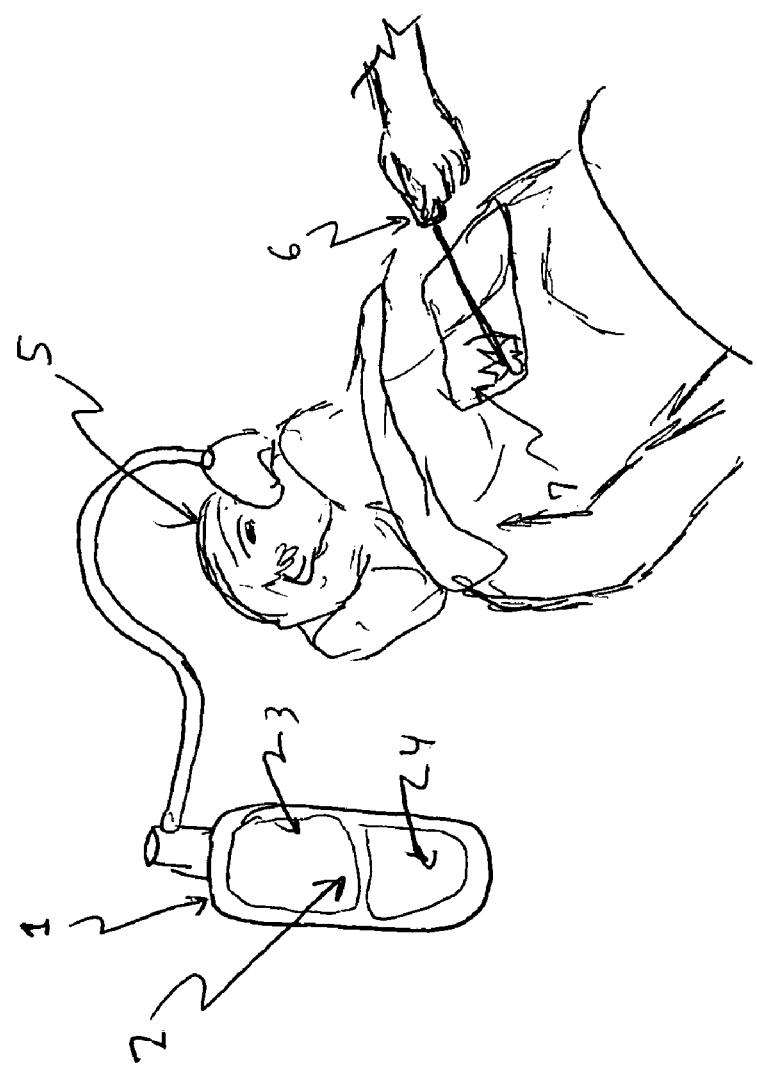
FIG. 1 is a view of the entire inert gas composition system, as used during a surgical procedure.

Refer to FIG. 1, view of the entire inert gas composition system, as applied in a surgical procedure. The system 1 comprises a container, hose and mask, said container enclosing an inert gas composition 2 containing oxygen 3 and an inert gas additive or combination of additives 4. It is directed into a patient 5 to be assisted during a medical procedure or for long term care. During a surgery event in this embodiment, a laser tool 6 has nicked the lung 7 of the patient and has come into contact with the inert gas composition 2. Since this composition is of a nature that will not support combustion, ignition and subsequent fire does not occur.

Other ignition scenarios can also occur, even in the operating room, due to leaking oxygen that collects under operating table curtains or sheets and ignites at remote ignition source sites. Such compositions, possibly with modified component gas ratios, are also suitable for home health care applications, in which nasal canula versus a mask are employed on the system. Other occupied space applications, such as manned outer space compartments or submarines as examples, are also suitable for such compositions to improve fire safety.

A few inert (in terms of inhibiting ignition of flammable substances) component gases have been identified currently that permit high exposure concentrations for humans with acceptable toxicity levels, such as sulfur hexafluoride or hydrofluoromethane. The most appealing class of compounds currently identified are the perfluorocarbons. These chemicals exhibit a very low toxicity characteristic, and high efficiency in inerting high oxygen concentrations.

One can establish the proper concentrations of candidate inertants with oxygen when applying the principle established by Huggett in determining the proper blends that reach the threshold bulk heat capacities from 40 (for less flammable materials in proximity) to 50 cal/C (for more flammable materials in proximity) that will not sustain combustion. Performing the calculations required, using the published heat capacities of oxygen and the various candidate inertants, it can be found that a blend of 54.5% perfluoropropane and 44.5% oxygen will reach the critical 50 cal/C threshold, permitting the use of high concentration oxygen suitable for medical applications. If a specific heat threshold of 40 cal/C is acceptable for the surrounding combustibles in question, then a blend of 48% perflouropropane and 52% oxygen is acceptably safe from combustion. It should be noted that these concentrations, and all other calculations in this disclosure, are on a volumetric or molar basis.

Other similar perfluorocarbon gases such as perfluoromethane and perfluoroethane also have similar inertion characteristics. Such gases can be obtained readily and economically (being used in large scale processes such as aluminum smelting and electronic chip processing), and blends can be mixed easily (since they are normally stored in compressed gas state) and distributed in specially designated canisters.

Perfluorocarbon chemicals are known for their remarkable molecular bond strength and stability under all but the most extreme environments (such as extremely high temperatures associated with pre-existing flames). As such, they are generally considered biologically inert, and any temporary bodily effects are those typically associated with oxygen deprivation, when very high concentrations (40% or higher) are added to normal air, where the oxygen concentration would drop enough such that effects would be due to the oxygen dilution predominantly. Such oxygen reduction is not an issue when the gases are added to a pre-existing 100% or high concentration oxygen blend beforehand. Published data generally shows no identified upper limits of perfluorocarbon exposure with no observed adverse effects, with the lowest published being a 40% concentration added to normal air, with the inherent oxygen reduction being the likely culprit of any observed effects.

If it is desired, for toxicity concerns or other issues, to reduce the concentration of perfluoropropane or any other primary inertant, it can be diluted with secondary inertants such as nitrogen. For example, a mixture of 31.2% oxygen, 30% perfluoropropane, and 38.8% nitrogen meets the 50 cal/C requirements of inertion, while for the 40 cal/C threshold an oxygen/perfluoropropane/nitrogen blend of 39%/30%/31% will suffice. It should be noted that this blend does not begin with the actual oxygen to nitrogen ratios of standard air; rather, it is a special blend starting with pure oxygen, then adding the required additives in proportion.

Another high-heat capacity inertant component of some merit and worthy of consideration is sulfur hexafluoride, or $SF_6$. If used alone with oxygen, it results in a blend of 31.2% oxygen and 64.8% sulfur hexafluoride for the 50 cal/C threshold, and for the 40 cal/C threshold a blend of 41.5% oxygen and 58.5% sulfur hexafluoride. A more optimal blend is established with perfluoropropane (with the presumption that it is restricted to 30% by volume); for the 50 cal/C threshold, an oxygen/perfluoropropane/sulfur hexafluoride blend of 40.8%/30.0%/29.2% is satisfactory, whereas for the 40 cal/C threshold a corresponding blend of 48.0%/30.0%/22% is sufficient.

Another ideal candidate is dodecafluoro-2-methylpentan-3-one, with the chemical formula $CF_3C(O)CF(CF_3)_2$. This candidate has a molar heat capacity even higher than perfluoropropane, and is commercially available. It has favorable environmental properties, but its NOAEL (No Observable Adverse Effects Limit) toxicity limit of 10% by volume limits it to a minor additive role in tertiary blends. However, when it ("additive") is added at that level to a blend of perfluoropropane and oxygen, for the 50 cal/C limit an oxygen/perflouropropane/additive volumetric ratio of 49.4%/40.6%/10.0% is adequate; for the 40 cal/C limit, a ratio of 56.6%/33.4%/10.0% is sufficient (at well over 50% oxygen concentration). This additive can even be used successfully with sulfur hexafluoride alone, resulting in an oxygen/sulfur hexafluoride/additive volumetric ratio of 41.10%/48.90%/10.0% for the 50 cal/C threshold, and 48.5%/41.5%/10.0% for the 40 cal/C threshold.

Other inerting gaseous chemicals may also be available now, or synthesized in the future, that can be employed in the configuration of this invention as alternative embodiments. Additionally, many other applications of a breathable, inert, high-oxygen concentration gas mix may be available. These could also include use in aircraft oxygen reservoirs for aircraft pilots, crew and passengers (with such reservoirs being inert from deflagration even when exposed to gunfire), firefighters and others that use air or oxygen canisters for their operation (including miners and other rescue personnel), astronauts, seamen (particularly submarine crew) and even race car drivers that might prefer a separate supply of high-oxygen gas to maintain mental acuity during long events, prevent exposure to carbon monoxide, and an provide independent breathing supply when exposed to noxious fumes while escaping a fire. Many other applications could also be possible.

Figure 2:
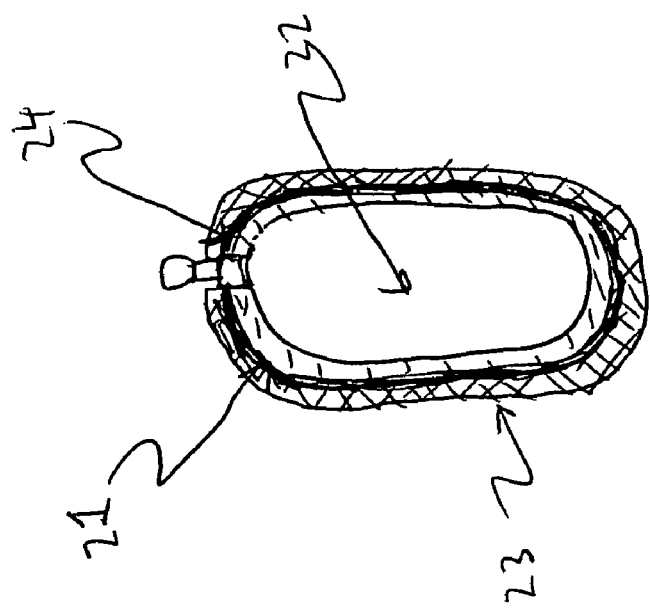
FIG. 2 is a side cutaway view of a container with a high oxygen blend, covered with a jacket or shroud.

Using such inertant combinations, there is also provided protection for the bottles to keep them from causing catastrophic fires resulting from impacts to them from collisions or from ballistic projectiles in combat, thereby rupturing the tanks and spilling their contents on ignition sources and combustibles nearby, while they are being transported, for example. Alternatively, FIG. 2 illustrates an alternative method of protection for an oxygen bottle, even if the inert blend is not filled within the bottle. In this embodiment, a hollow jacket or shroud 23 is placed around the oxygen bottle 21, which is filled with oxygen or inert blend 22. Within the hollow space inside the jacket/shroud is a void area 24, filled with the inert blend. In the event of a rupture to the bottle, the outer jacket/shroud is also ruptured, dispersing the inertant to mix with the oxygen released from the bottle to prevent fires. In this case, the inertant blend does not have to be mixed with oxygen beforehand. The jacket/shroud can be permanently attached to the bottle, or removable and attached only during shipment.

There is thus described novel techniques and features to provide a breathable, inert mixture of gases containing high oxygen concentrations and a system to deliver it, which meets all of its stated objectives and which overcomes the disadvantages of existing techniques.

The foregoing description of the preferred embodiments of the invention has been presented for purposes of illustration and description. It is not intended to be exhaustive or limit the invention to the precise form disclosed. Many modifications and variations are possible in light of the above teaching. It is intended that the scope of the invention be limited not by this detailed description, but rather by the claims appended hereto.

I claim:

1. A method of preventing fires resulting from the use of oxygen delivery systems in proximity to ignition sources and combustible materials, said method comprising the steps of
   a) preparing a blend of oxygen and inert gas components of sufficient heat capacity to prevent ignition of combustibles in its region of release,
   b) disposing said blend within an oxygen delivery container with delivery apparatus, and
   c) administering said blend to a recipient through said delivery apparatus,
   said blend comprising a composition of gases having an oxygen/nitrogen/perfluoropropane/sulfur hexafluoride/dodecafluoro-2-methylpentan-3-one volumetric ratio selected from the group consisting of:
   44.5/0/54.5/0/0,
   52.0/0/48.0/0/0,
   31.2/38.8/30.0/0/0,
   39.0/31.0/30.0/0/0,
   31.2/0/0/64.8/0,
   41.5/0/0/58.5/0,
   40.8/0/30.0/29.2/0,
   48.0/0/30.0/22.0/0,
   49.4/0/40.6/0/10.0,
   56.6/0/33.4/0/10.0,
   41.1/0/0/48.9/10.0, and
   48.5/0/0/41.5/10.0.

2. A system for preventing fires resulting from the use of oxygen delivery systems in proximity to ignition sources and combustible materials, said system comprising
   a) an oxygen delivery container with attached delivery apparatus,
   b) a blend of oxygen and inert gases of sufficient bulk heat capacity to prevent the ignition of combustibles in its region of release, disposed within said container, and
   c) a recipient for said blend through said delivery apparatus, said blend comprising a composition of gases comprising at least 30 percent volumetric concentration of oxygen and individual constituent gases defined in their relative ratios by a range of respective volumetric concentrations selected from the group of constituent combination ratios consisting of:
   more than zero and up to 39.5 percent nitrogen and 30.5 to less than 70 percent sulfur hexafluoride,
   58 to 61.5 percent nitrogen and 8.5 to 10 percent dodecafluoro-2-methylpentan-3-one,
   3.5 to 50 percent hydrofluoromethane and 13.5 to 40 percent perfluorobutane,
   18.5 to less than 70 percent sulfur hexafluoride and more than zero and up to 50 percent hydrofluoromethane,
   30 to 40 percent perfluorobutane and 1.5 to 10 percent dodecafluoro-2-methylpentan-3-one, greater than zero to 10 percent dodecafluoro-2-methylpentan-3-one and 41 to less than 70percent sulfur hexafluoride,
   greater than zero to 56 percent nitrogen, greater than zero to 64.5 percent hydrofluoromethane, and greater than 4.5 to 40 percent perfluorobutane,
   3.5 to less than 61.5 percent nitrogen, greater than zero to 50 percent hydrofluoromethane, and 4 to 9 percent dodecafluoro-2-methylpentan-3-one,
   greater than zero to less than 40 percent nitrogen, greater than zero to 50 percent hydrofluoromethane, and 15 to less than 70 percent sulfur hexafluoride,
   greater than zero to 57 percent nitrogen, greater than zero to 40 percent perfluorobutane, and greater than zero to 10 percent dodecafluoro-2-methylpentan-3-one,
   greater than zero to less than 60 percent nitrogen, greater than zero to 10 percent dodecafluoro-2-methylpentan-3-one, and greater than zero to 70 percent sulfur hexafluoride,
   greater than zero to 67.5 percent hydrofluoromethane, greater than zero to 40 percent perfluorobutane, and greater than zero to 10 percent dodecafluoro-2-methylpentan-3-one,
   greater than zero to 50 percent hydrofluoromethane, greater than zero to 40 percent perfluorobutane, and greater than zero to less than 70 percent sulfur hexafluoride,
   greater than zero to 50 percent hydrofluoromethane, greater than zero to 10 percent dodecafluoro-2-methylpentan-3-one and one to less than 70 percent sulfur hexafluoride,
   greater than zero to 40 percent perfluorobutane, greater than zero to 10 percent dodecafluoro-2-methylpentan-3-one, and greater than zero to less than 70 percent sulfur hexafluoride,
   greater than zero to 61.5 percent nitrogen, greater than zero to 50 percent hydrofluoromethane,
   greater than zero to 40 percent perfluorobutane, and greater than zero 10 percent dodecafluoro-2-methylpentan-3 -one,
   greater than zero to less than 57 percent nitrogen, greater than zero to 50 percent hydrofluoromethane, greater than zero to 40 percent perfluorobutane, and greater than zero to less than 70 percent sulfur hexafluoride,
   greater than zero to less than 61.5 percent nitrogen, greater than zero to 50 percent hydrofluoromethane, greater than zero to 10 percent dodecafluoro-2-methylpentan-3-one, and greater than zero to less than 70 percent sulfur hexafluoride,
   greater than zero to less than 61.5 percent nitrogen, greater than zero to 40 percent perfluorobutane, greater than zero to 10 percent dodecafluoro-2-methylpentan-3-one, and greater than zero to less than 70 percent sulfur hexafluoride,
   greater than zero to 50 percent hydrofluoromethane, greater than zero to 40 percent perfluorobutane, greater than zero to 10 percent dodecafluoro-2-methylpentan-3-one, and greater than zero to less than 70 percent sulfur hexafluoride, greater than zero to 61.5 percent nitrogen, greater than zero to 50 percent hydrofluoromethane, greater than zero to 40 percent perfluorobutane, greater than zero to 10 percent dodecafluoro-2-methylpentan-3-one, and greater than zero to less than 70 percent sulfur hexafluoride, 31 to 52.5 percent nitrogen and 17.5 to 30 percent perfluoropropane, 40 to 50 percent hydrofluoromethane and 15.5 to 30 percent perfluoropropane, greater than zero to 30 percent perfluoropropane and 40 to less than 70 percent sulfur hexafluoride, greater than zero to 52.5 percent nitrogen, greater than zero to 50 percent hydrofluoromethane, and greater than zero to 30 percent perfluoropropane, greater than 5.5 to less than 61.5 percent nitrogen, greater than zero to 30 percent perfluoropropane, and greater than zero to 10 percent dodecafluoro-2-methylpentan-3-one, greater than zero to 52.5 percent nitrogen, greater than zero to 30 percent perfluoropropane, and greater than zero to less than 70 percent sulfur hexafluoride, 30 to 50 percent hydrofluoromethane, 10 to 30 percent perfluoropropane, and greater than zero to 10 percent dodecafluoro-2-methylpentan-3-one, greater than zero to 50 percent hydrofluoromethane, greater than zero to 30 percent perfluoropropane, and greater than zero to less than 70 percent sulfur hexafluoride, greater than zero to 30 percent perfluorobutane, greater than zero to 10 percent dodecafluoro-2-methylpentan-3-one, and 4.5 to less than 70 percent sulfur hexafluoride, greater than zero to 61.5 percent nitrogen, greater than zero to 50 percent hydrofluoromethane, greater than zero to 30 percent perfluoropropane, and greater than zero to 10 percent dodecafluoro-2-methylpentan-3-one, greater than zero to less than 52.5 percent nitrogen, greater than zero to 50 percent hydrofluoromethane, greater than zero to 30 percent perfluoropropane, and greater than zero to less than 70 percent sulfur hexafluoride, greater than zero to less than 61.5 percent nitrogen, greater than zero to 30 percent perfluoropropane, greater than zero to 10 percent dodecafluoro-2-methylpentan-3-one, and greater than zero to less than 70 percent sulfur hexafluoride, greater than zero to 50 percent hydrofluoromethane, greater than zero to 30 percent perfluoropropane, greater than zero to 10 percent dodecafluoro-2-methylpentan-3-one, and greater than zero to less than 70 percent sulfur hexafluoride, and greater than zero to 61.5 percent nitrogen, greater than zero to 50 percent hydrofluoromethane, greater than zero to 30 percent perfluoropropane, greater than zero to 10 percent dodecafluoro-2-methylpentan-3-one, and greater than zero to less than 70 percent sulfur hexafluoride.

3. The system of claim 2, said blend of said system further comprising at least 30 percent volumetric concentration of oxygen and individual constituent gases defined in their relative ratios by a range of respective volumetric concentrations selected from the group of constituent combination ratios consisting of:

greater than zero to 9 percent hydrofluorocarbon and 48 to less than 70 percent sulfur hexafluoride, greater than zero to 9 percent hydrofluorocarbon and 34 to 40 percent perfluorobutane, greater than zero to 40 percent perfluorobutane, greater than zero to 9 percent hydrofluorocarbon, and greater than zero to less than 70 percent sulfur hexafluoride, greater than zero to 44 percent nitrogen, greater than zero to 9 percent hydrofluorocarbon, and 17 to less than 70 percent sulfur hexafluoride, 7 to 40 percent perfluorobutane, greater than zero to 54 percent nitrogen, and greater than zero to 9 percent hydrofluorocarbon, greater than zero to 57 percent nitrogen, greater than zero to 40 percent perfluorobutane, greater than zero to 9 percent hydrofluorocarbon, and greater than zero to less than 70 percent sulfur hexafluoride, 43 to 61 percent nitrogen, greater than zero to 9 percent hydrofluorocarbon, and 4.5 to 10 percent dodecafluoro-2-methylpentan-3-one, 21 to 50 percent hydrofluoromethane, 6 to 40 percent perfluorobutane, and greater than zero to 9percent hydrofluorocarbon, 38 to 50 percent hydrofluoromethane, 1 to 9 percent hydrofluorocarbon and 4.5 to 10 percent dodecafluoro-2-methylpentan-3-one, greater than zero to 50 percent hydrofluoromethane, greater than zero to 9 percent hydrofluorocarbon, and 8 to less than 70 percent sulfur hexafluoride, 22 to 40 percent perfluorobutane, greater than zero to 9 percent hydrofluorocarbon, and greater than zero to 10 percent dodecafluoro-2-methylpentan-3-one, greater than zero to 9 hydrofluorocarbon, greater than zero to 10 percent dodecafluoro-2-methylpentan-3-one, and 30.5 to less than 70 percent sulfur hexafluoride, greater than zero to less than 57 percent nitrogen, greater than zero to 50 percent hydrofluoromethane, greater than zero to 40 percent perfluorobutane, and greater than zero to 10 percent dodecafluoro-2-methylpentan-3-one, greater than zero to less than 61.5 percent nitrogen, greater than zero to 50 percent hydrofluoromethane, greater than zero to 9 percent hydrofluorocarbon, and 1 to 10 percent dodecafluoro-2-methylpentan-3-one, greater than zero to less than 61.5 percent nitrogen, greater than zero to 40 percent perfluorobutane, greater than zero to 9 percent hydrofluorocarbon, and greater than zero to 10 percent dodecafluoro-2-methylpentan-3-one, greater than zero to 50 percent hydrofluoromethane, greater than zero to 40 percent perfluorobutane, greater than zero to 9 percenthydrofluorocarbon, and greater than zero to 10 percent dodecafluoro-2-methylpentan-3-one, greater than zero to 50 percent hydrofluoromethane, greater than zero to 40 percent perfluorobutane, greater than zero to 9 percent hydrofluorocarbon, and greater than zero to less than 70 percent sulfur hexafluoride, greater than zero to 44.5 percent nitrogen, greater than zero to 50 percent hydrofluoromethane, greater than zero to 9 percent hydrofluorocarbon, and 1 to less than 70 percent sulfur hexafluoride, greater than zero to less than 61.5 percent nitrogen, greater than zero to 9 percent hydrofluorocarbon, greater than zero to 10 percent dodecafluoro-2-methylpentan-3-one, and greater than zero to less than 70 percent sulfur hexafluoride, greater than zero to 50 percent hydrofluoromethane, greater than zero to 9 percent hydrofluorocarbon, greater than zero to 10 percent dodecafluoro-2-methylpentan-3-one, and
greater than zero to less than 70 percent sulfur hexafluoride,
greater than zero to 40 percent perfluorobutane, greater than zero to 9 percent hydrofluorocarbon, greater than zero to 10 percent dodecafluoro-2-methylpentan-3-one and
greater than zero to less than 70 percent sulfur hexafluoride,
greater than zero to less than 57 percent nitrogen, greater than zero to 50 percent hydrofluoromethane greater than zero to 40 percent perfluorobutane, greater than zero to 9 percent hydrofluorocarbon, and greater than zero to 10 percent dodecafluoro-2-methylpentan-3-one,
greater than zero to less than 57 percent nitrogen, greater than zero to 50 percent hydrofluoromethane, greater than zero to 40 percent perfluorobutane, greater than zero to 9 percent hydrofluorocarbon, and greater than zero to less than 70 percent sulfur hexafluoride,
greater than zero to less than 61.5 percent nitrogen, greater than zero to 50 percent hydrofluoromethane, greater than zero to 9 hydrofluorocarbon, greater than zero to 10 percent dodecafluoro-2-methylpentan-3-one, and greater than zero to less than 70 percent sulfur hexafluoride,
greater than zero to less than 57 percent nitrogen, greater than zero to 40 percent perfluorobutane, greater than zero to 9 percent hydrofluorocarbon, greater than zero to 10 percent dodecafluoro-2-methylpentan-3-one, and greater than zero to less than 70 percent sulfur hexafluoride,
greater than zero to 50 percent hydrofluoromethane, greater than zero to 40 percent perfluorobutane, greater than zero to 9 percent hydrofluorocarbon, greater than zero to 10 percent dodecafluoro-2-methylpentan-3-one, and greater than zero to less than 70 percent sulfur hexafluoride,
greater than zero to 59 percent nitrogen, greater than zero to 50 percent hydrofluoromethane,
greater than zero to 40 percent perfluorobutane, greater than zero to 9 percent hydrofluorocarbon,
greater than zero to 10 percent dodecafluoro-2-methylpentan-3-one, and greater than zero to less than 70 percent sulfur hexafluoride,
greater than zero to 30 percent perfluoropropane, greater than zero to 9 percent hydrofluorocarbon, and 11.5 to less than 70 percent sulfur hexafluoride,
16.5 to 52.5 percent nitrogen, 9.5 to 30 percent perfluoropropane, and greater than zero to 9 percent hydrofluorocarbon,
greater than zero to 52.5 percent nitrogen, greater than zero to 30 percent perfluoropropane,
greater than zero to 9 percent hydrofluorocarbon, and greater than zero to less than 70 percent sulfur hexafluoride,
14.5 to 50 percent hydrofluoromethane, 6.5 to 30 percent perfluoropropane, and greater than zero to 9 percent hydrofluorocarbon,
greater than zero to 52.5 percent nitrogen, greater than zero to 50 percent hydrofluoromethane, 0.5 to 30 percent perfluoropropane, and greater than zero to 9 percent hydrofluorocarbon,
greater than zero to 61.5 percent nitrogen, greater than zero to 30 percent perfluoropropane, greater than zero to 9 percent hydrofluorocarbon, and greater than zero to 10 percent dodecafluoro-2-methylpentan-3-one,
greater than zero to 50 percent hydrofluoromethane, greater than zero to 30 percent perfluoropropane, greater than zero to 9 percent hydrofluorocarbon, and greater than zero to 10 percent dodecafluoro-2-methylpentan-3-one,
greater than zero to 50 percent hydrofluoromethane, greater than zero to 30 percent perfluoropropane, greater than zero to 9 percent hydrofluorocarbon, and greater than zero to less than 70 percent sulfur hexafluoride,
greater than zero to 30 percent perfluoropropane, greater than zero to 9 percent hydrofluorocarbon, greater than zero to 10 percent dodecafluoro-2-methylpentan-3-one, and
greater than zero to less than 70 percent sulfur hexafluoride,
greater than zero to 61.5 percent nitrogen, greater than zero to 50 percent hydrofluoromethane,
greater than zero to 30 percent perfluoropropane, greater than zero to 9 percent hydrofluorocarbon, and greater than zero to 10 percent dodecafluoro-2-methylpentan-3-one,
greater than zero to 52.5 percent nitrogen, greater than zero to 50 percent hydrofluoromethane,
greater than zero to 30 percent perfluoropropane, greater than zero to 9 percent hydrofluorocarbon, and greater than zero to less than 70 percent sulfur hexafluoride,
greater than zero to 50 percent hydrofluoromethane, greater than zero to 30 percent perfluoropropane, greater than zero to 9 percent hydrofluorocarbon, greater than zero to 10 percent dodecafluoro-2-methylpentan-3-one, and greater than zero to less than 70 percent sulfur hexafluoride, and
greater than zero to less than 61.5 percent nitrogen, greater than zero to 50 percent hydrofluoromethane, greater than zero to 30 percent perfluoropropane, greater than zero to 9 percent hydrofluorocarbon, greater than zero to 10 percent dodecafluoro-2-methylpentan-3-one, and greater than zero to less than 70 percent sulfur hexafluoride,
wherein "hydrofluorocarbon" is defined to comprise at least one selected from a group of
pentafluoroethane,
heptafluoropropane and
hexafluoropropane.

4. The system of claim 2, said blend of said system further comprising a composition having an oxygen/nitrogen/perflourobutane/perfluoropropane/perfluoroethane/sulfur hexafluoride/dodecafluoro-2-methylpentan-3-one/hydrofluoromethane/hydrofluorocarbon volumetric ratio selected from the group consisting of:
41/1/0/0/0/58/0/0/0,
32/58/0/0/0/0/10/0/0,
56.5/0140/0/0/0/0/3.5/0,
41/0/0/0/0/58/0/1/0,
60.5/0/29.5/0/0/0/10/0/0,
49/0/0/0/0/41/10/0/0,
56/1/40/0/0/0/0/3/0,
39/1/0/0/0/0/10/50/0,
41/1/0/0/0/57/0/1/0,
60/1/29/0/0/0/10/0/0,
48.5/1/0/0/0/40.5/10/0/0,
60/0/29/0/0/0/10/1/0,
57/0/40/0/0/2/0/1/0,
49/0/0/0/0/40/10/1/0, 60.5/0/28.5/0/0/1/10/0/0,
59.5/1/28.5/0/0/0/10/1/0,
56.5/1/40/0/0/1.5/0/1/0,
48.5/1/0/0/0/39.5/10/1/0,
60/1/28/0/0/1/10/0/0,
60/0/28/0/0/1/10/1/0,
59.5/1/27.5/0/0/1/10/1/0,
39/0/0/0/0/0/10/51/0,
39/31/0/30/0/0/0/0/0,
42.5/0/0/30/0/0/0/27.5/0,
48/0/0/30/0/0/22/0/0/0,
42/1/0/30/0/0/0/27/0,
53.5/6.5/0/30/0/0/10/0/0,
47.5/1/0/30/0/21.5/0/0/0,
54.5/0/0/30/0/0/10/5.5/0,
47.5/0/0/30/0/21.5/0/1/0,
55.5/0/0/30/0/4.5/10/0/0,
54.5/1/0/30/0/0/10/4.5/0,
47.5/1/0/30/0/20.5/0/1/0,
55.5/1/0/30/0/3.5/10/0/0,
55.5/0/0/30/0/3.5/10/1/0, and
55/1/0/30/0/3/10/1/0,
wherein "hydrofluorocarbon" is defined to comprise at least one selected from the group consisting of:
pentafluoroethane,
heptafluoropropane, and
hexafluoropropane.

5. The system of claim 2, said blend of said system further comprising a composition having an
oxygen/nitrogen/perflourobutane/perfluoropropane/perfluoroethane/sulfur hexafluoride/dodecafluoro-2-methylpentan-3-one/hydrofluoromethane/hydrofluorocarbon volumetric ratio selected from the group consisting of:
43/0/0/0/0/48/0/019,
57.5/0/40/0/0/0/0/0/2.5,
57.5/0/40/0/0/1/0/0/1.5,
42.5/1/0/0/0/47.5/0/0/9,
57/1/40/0/0/0/0/0/2,
57/1/40/0/0/1/0/0/1,
38/43/0/0/0/0/10/0/9,
57/0/40/0/0/0/0/1/2,
43/0/0/0/0/0/10/38/9,
42.5/0/0/0/0/47.5/0/1/9,
61/0/29/0/0/0/10/0/1,
50.5/0/0/0/0/30.5/10/0/9,
57/1/40/0/0/0/0/1/1,
43/1/0/0/0/0/10/37/9,
60/1/28/0/0/0/10/0/1,
60/0/28/0/0/0/10/1/1,
57/0/40/0/0/1/0/1/1,
42.5/1/0/0/0/46.5/0/1/9,
50/1/0/0/0/30/10/0/9,
50.5/0/0/0/0/29.5/10/1/9,
60/0/28/0/0/1/10/0/1,
59.5/1/27.5/0/0/0/10/1/1,
56.5/1/40/0/0/1/0/1/0.5,
50/1/0/0/0/29/10/1/9,
59.5/1/27.5/0/0/1/10/0/1,
59.5/0/27.5/0/0/1/10/1/1,
59/1/27/0/0/1/10/1/1,
49.5/0/0/30/0/11.5/0/0/9,
44.5/16.5/0/30/0/0/0/0/9,
49/1/0/30/0/11/0/0/9,
46.5/0/0/30/0/0/0/14.5/9,
46.5/1/0/30/0/0/0/13.5/9,
56/1/0/30/0/0/0/10/0/3,
56/0/0/30/0/0/10/1/3,
49/0/0/30/0/11/0/1/9,
56/0/0/30/0/1/10/0/3,
55.5/1/0/30/0/0/0/10/1/2.5,
49/1/0/30/0/10/0/1/9,
55.5/0/0/30/0/1/10/1/2.5, and
55/1/0/30/0/1/10/1/1.5,
wherein "hydrofluorocarbon" is defined to comprise at least one selected from a group of
pentafluoroethane,
heptafluoropropane and
hexafluoropropane.

6. The system of claim 2, said blend of said system further comprising a composition having an
oxygen/nitrogen/perflourobutane/perfluoropropane/perfluoroethane/sulfur hexafluoride/dodecafluoro-2-methylpentan-3-one/hydrofluoromethane/hydrofluorocarbon volumetric ratio selected from the group consisting of:
37.5/1/0/0/0/61.5/0/0/0,
28.5/61.5/0/0/0/0/10/0/0,
51/0/40/0/0/0/0/9/0,
37.5/0/0/0/0/61.5/0/1/0,
57/0/33/0/0/0/10/0/0,
45/0/0/0/0/45/10/0/0,
50.5/1/40/0/0/0/0/8.5/0,
34.5/5.5/0/0/0/0/10/50/0,
37.5/1/0/0/0/60.5/0/1/0,
56.5/1/32.5/0/0/0/10/0/0,
45/1/0/0/0/0/44/10/0/0,
56.5/0/32.5/0/0/0/10/1/0,
52/0/40/0/0/7/0/1/0,
45/0/0/0/0/44/10/1/0,
56.5/0/32.5/0/0/1/10/0/0,
56/1/32/0/0/0/10/1/0,
52/1/40/0/0/6/0/1/0,
44.5/1/0/0/0/43.5/10/1/0,
56/1/32/0/0/1/10/0/0,
56.5/0/31.5/0/0/1/10/1/0,
56/1/31/0/0/1/10/1/0,
35/0/0/0/0/0/10/55/0,
34.5/35.5/0/30/0/0/0/0/0,
38/0/0/30/0/0/0/32/0,
44/0/0/30/0/26/0/0/0,
38/1/0/30/0/0/0/31/0,
48/12/0/30/0/0/10/0/0,
43.5/1/0/30/0/25.5/0/0/0,
49/0/0/30/0/0/10/11/0,
43.5/0/0/30/0/25.5/0/1/0,
51/0/0/30/0/9/10/0/0,
49/1/0/30/0/0/10/10/0,
43.5/1/0/30/0/24.5/0/1/0,
51/1/0/30/0/8/10/0/0,
51/0/0/30/0/8/10/1/0, and
50.5/1/0/30/0/7.5/1 0/1/0,
wherein "hydrofluorocarbon" is defined to comprise at least one selected from the group consisting of:
pentafluoroethane,
heptafluoropropane, and
hexafluoropropane.

7. The system of claim 2, said blend of said system further comprising a composition having an
oxygen/nitrogen/perflourobutane/perflouropropane/perflouroethane/sulfur hexafluoride/dodecafluoro-2-methylpentan-3-one/hydrofluoromethane/hydrofluorocarbon volumetric ratio selected from the group consisting of:

39.5/0/0/0/0/51.5/0/0/9,
53.5/0/40/0/0/0/0/0/6.5,
53.5/0/40/0/0/1/0/0/5.5,
39/1/0/0/0/51/0/0/9,
53/1/40/0/0/0/0/0/6,
53/1/40/0/0/1/0/0/5,
34/47/0/0/0/0/10/0/9,
53/0/40/0/0/0/0/1/6,
39/0/0/0/0/0/10/42/9,
39/0/0/0/0/51/0/1/9,
57/0/32/0/0/0/10/0/1,
46.5/0/0/0/0/34.5/10/0/9,
52.5/1/40/0/0/0/0/1/5.5,
38.5/1/0/0/0/0/10/41.5/9,
56.5/1/31.5/0/0/0/10/0/1,
56.5/0/31.5/0/0/0/10/1/1,
53/0/40/0/0/1/0/1/5,
38/1/0/0/0/51/0/1/9,
46/1/0/0/0/34/10/0/9,
46/0/0/0/0/34/10/1/9,
56.5/0/31.5/0/0/1/10/0/1,
56/1/31/0/0/0/10/1/1,
52.5/1/40/0/0/1/0/1/4.5,
46/1/0/0/0/33/10/1/9,
56/1/31/0/0/1/10/0/1,
56/0/31/0/0/1/10/1/1,
55.5/1/30.5/0/0/1/10/1/1,
45.5/0/0/30/0/15.5/0/0/9,
39.5/21.5/0/30/0/0/0/0/9,
45/1/0/30/0/15/0/0/9,
42/0/0/30/0/0/0/19/9,
41.5/1/30/0/0/0/0/18.5/9,
52/1/0/30/0/0/10/0/7,
52/0/0/30/0/0/10/1/7,
45/0/0/30/0/15/0/1/9,
52/0/0/30/0/1/10/0/7,
51.5/1/0/30/0/0/10/1/6.5,
45/1/0/30/0/14/0/1/9,
52/0/0/30/0/1/10/1/6, and
51.5/1/0/30/0/1/10/1/5.5,
wherein "hydrofluorocarbon" is defined to comprise at least one selected from the group consisting of:
pentafluoroethane,
heptafluoropropane, and
hexafluoropropane.

8. The system of claim 2, said blend of said system further comprising a composition having an
oxygen/nitrogen/perflourobutane/perfluoropropane/perfluoroethane/sulfur hexafluoride/dodecafluoro-2-methylpentan-3-one/hydrofluoromethane/hydrofluorocarbon volumetric ratio selected from the group consisting of:
35/1/0/0/0/64/0/0/0,
30/60/0/0/0/0/10/0/0,
46/0/40/0/0/0/0/14/0,
35/0/0/0/0/64/0/1/0,
53.5/0/36.5/0/0/0/10/0/0,
41.5/0/0/0/0/48.5/10/0/0,
46/1/40/0/0/0/0/13/0,
31/9/0/0/0/0/1 0/50/0,
34.5/1/0/0/0/63.5/0/1/0,
53.5/1/35.5/0/0/0/10/0/0,
41.5/1/0/0/0/47.5/10/0/0,
53.5/0/35.5/0/0/0/10/1/0,
48.5/0/40/0/0/0/10.5/0/1/0,
41.5/0/0/0/0/47.5/10/1/0,
53.5/0/35.5/0/0/1/10/0/0,
53/1/35/0/0/0/10/1/0,
48/1/40/0/0/0/10/0/1/0,
41/1/0/0/0/47/10/1/0,
53/1/35/0/0/1/10/0/0,
53/0/35/0/0/1/10/1/0,
52.5/1/34.5/0/0/1/10/1/0,
35/0/0/0/0/0/10/55/0,
31/39/0/30/0/0/0/0/0,
34.5/0/0/30/0/0/0/35.5/0,
40.5/0/0/30/0/29.5/0/0/0,
34.5/1/0/30/0/0/0/34.5/0,
43/17/0/30/0/0/10/0/0,
40.5/1/0/30/0/28.5/0/0/0,
44.5/0/0/30/0/0/10/15.5/0,
40.5/0/0/30/0/28.5/0/1/0,
47/0/0/30/0/13/10/0/0,
44.5/1/0/30/0/0/10/14.5/0,
40/1/0/30/0/28/0/1/0,
47/1/0/30/0/12/10/0/0,
47/0/0/30/0/12/10/1/0, and
46.5/1/0/30/0/11.5/10/1/0,
wherein "hydrofluorocarbon" is defined to comprise at least one selected from the group consisting of:
pentafluoroethane,
heptafluoropropane, and
hexafluoropropane.

9. The system of claim 2, said blend of said system further comprising a composition having an
oxygen/nitrogen/perflourobutane/perfluoropropane/perfluoroethane/sulfur hexafluoride/dodecafluoro-2-methylpentan-3-one/hydrofluoromethane/hydrofluorocarbon volumetric ratio selected from the group consisting of:
36.5/0/0/0/0/54.5/0/0/9,
51/0/40/0/0/0/0/0/9,
50/0/40/0/0/1/0/0/9,
36/1/0/0/0/54/0/0/9,
49.5/1.5/40/0/0/0/0/0/9,
49.5/1/40/0/0/1/0/0/8.5,
30.5/50.5/0/0/0/0/10/0/9,
49.5/0/40/0/0/0/0/1.5/9,
35/0/0/0/0/0/10/46/9,
36/0/0/0/0/54/0/1/9,
53.5/0/35.5/0/0/0/10/0/1,
43/0/0/0/0/38/10/0/9,
49.5/1/40/0/0/0/0/1/8.5,
35/1/0/0/0/0/10/45/9,
53/1/35/0/0/0/10/0/1,
53/0/35/0/0/0/10/1/1,
49.5/0/40/0/0/1/0/1/8.5,
36/1/0/0/0/53/0/1/9,
42.5/1/0/0/0/37.5/10/0/9,
42.5/0/0/0/0/37.5/10/1/9,
53.5/0/34.5/0/0/0/1/10/0/1,
53/1/34/0/0/0/10/1/1,
49/1/40/0/0/1/0/1/8,
42.5/1/0/0/0/36.5/10/1/9,
53/1/34/0/0/1/10/0/1,
53/0/34/0/0/1/10/1/1,
52.5/1/33.5/0/0/1/10/1/1,
42/0/0/30/0/19/0/0/9,
35.5/25.5/0/30/0/0/0/0/9,
41.5/1/0/30/0/18.5/0/0/9,
38/0/0/30/0/0/0/23/9,
38/1/0/30/0/0/0/22/9,
47.5/3.5/0/30/0/0/10/0/9,
48/0/0/30/0/0/10/3/9, 41.5/0/0/30/0/18.5/0/1/9,
48.5/0/0/30/0/2.5/10/0/9,
48/1/0/30/0/0/10/2/9,
41.5/1/0/30/0/17.5/0/1/9,
48.5/0/0/30/0/1.5/10/1/9, and
48/1/0/30/0/1/10/1/9, wherein "hydrofluorocarbon" is defined to comprise at least one selected from the group consisting of:
pentafluoroethane,
heptafluoropropane, and
hexafluoropropane.

10. The system of claim 2, wherein said system is specified for use for said recipient selected from the group consisting of:
a surgery patient,
a hospitalized non-surgical patient,
a recipient at a site remote from a medical care facility,
a pilot,
an aircraft passenger,
a fireman,
a miner,
an astronaut,
a seaman, and
a race car driver.

11. The system of claim 2, wherein said blend of said system is administered to said recipient using a delivery apparatus selected from the group consisting of an oxygen mask and a nasal canula.

12. A system for preventing fires resulting from the use of oxygen delivery systems in proximity to ignition sources and combustible materials, said system comprising
a) an oxygen delivery container with attached delivery apparatus,
b) a blend of oxygen and inert gases of sufficient bulk heat capacity to prevent the ignition of combustibles in its region of release, disposed within said container, and
c) a recipient for said blend through said delivery apparatus, said blend comprising a composition of gases, comprising:
a) oxygen of at least 30 percent in volumetric concentration, and
b) at least one gas selected from the group consisting of:
dodecafluoro-2-methylpentan-3-one, and
hydrofluoromethane,
wherein said composition has a heat capacity of at least 40 cal/(C mol $O_2$), and each constituent gas of said composition being present in volumetric concentrations such that acceptable the NOAEL human inhalation toxicity concentration thresholds respective to each gas constituent are not exceeded.

13. The system of claim 12, wherein said blend of said system further comprises at least one gas selected from the group consisting of:
nitrogen, and
sulfur hexafluoride.

14. The system of claim 12, wherein said blend of said system further comprises at least one gas selected from the group consisting of:
heptafluoropropane,
hexafluoropropane,
pentafluoromethane, and
helium.

15. The system of claim 12, wherein said blend of said system further comprises at least one gas selected from the group consisting of:
perfluorobutane,
perfluoropropane,
perfluoroethane, and
perfluoromethane.

16. The system of claim 12, wherein said blend of said system is further restricted to a heat capacity of at least 45 cal/(C mol $O_2$).

17. The system of claim 12, wherein said blend of said system is further restricted to a heat capacity of at least 50 cal/(C mol $O_2$).

18. The system of claim 12, wherein said oxygen concentration of said blend of said system is further restricted to a volumetric concentration of at least 55.8 percent.

19. The system of claim 12, wherein said system is specified for use for a said recipient selected from a list consisting of a
surgery patient,
hospitalized non-surgical patient,
a recipient at a site remote from a medical care facility,
a pilot,
an aircraft passenger,
a fireman,
a miner,
an astronaut,
a seaman and
a race car driver.

20. The system of claim 12, wherein said blend of said system is administered to a said recipient using a delivery apparatus selected from the group consisting of an oxygen mask and a nasal canula.

* * * * *